(12) United States Patent
Rulison et al.

(10) Patent No.: US 7,518,726 B2
(45) Date of Patent: Apr. 14, 2009

(54) COMPACT OPTICAL DETECTION SYSTEM FOR A MICROFLUIDIC DEVICE

(75) Inventors: Aaron Rulison, Los Altos, CA (US); Jeffrey A. Wolk, Half Moon Bay, CA (US); Ernest C.W. Lee, Palo Alto, CA (US); Michael Slater, Modesto, CA (US); Morten J. Jensen, San Francisco, CA (US)

(73) Assignee: Caliper LifeSciences, Inc., Mountain View, CA (US)

( * ) Notice: Subject to any disclaimer, the term of this patent is extended or adjusted under 35 U.S.C. 154(b) by 365 days.

(21) Appl. No.: 11/404,043

(22) Filed: Apr. 12, 2006

(65) Prior Publication Data

US 2006/0227325 A1    Oct. 12, 2006

Related U.S. Application Data

(60) Provisional application No. 60/670,736, filed on Apr. 12, 2005.

(51) Int. Cl.
*G01B 11/00* (2006.01)
(52) U.S. Cl. ............................. 356/401; 356/246
(58) Field of Classification Search ................. 356/626, 356/399, 400, 401, 244, 246; 436/180, 164–165, 436/174; 422/58, 68.1, 81, 100–102
See application file for complete search history.

(56) References Cited

U.S. PATENT DOCUMENTS

| | | | |
|---|---|---|---|
| 5,539,764 A * | 7/1996 | Shields et al. | 372/57 |
| 6,008,892 A | 12/1999 | Kain | |
| 6,515,753 B2 | 2/2003 | Maher | |
| 6,985,224 B2 | 1/2006 | Hart | |
| 7,015,450 B2 | 3/2006 | Mikhailov | |
| 7,033,910 B2 * | 4/2006 | Faris | 438/455 |
| 2003/0008411 A1 * | 1/2003 | Van Dam et al. | 436/174 |
| 2003/0015672 A1 | 1/2003 | Gallagher | |
| 2003/0058445 A1 | 3/2003 | Fritz | |
| 2003/0127610 A1 * | 7/2003 | Gallagher | 250/574 |
| 2004/0014239 A1 * | 1/2004 | Wolk et al. | 436/180 |
| 2005/0225764 A1 | 10/2005 | Bacarase-Hamilton | |
| 2006/0078807 A1 * | 4/2006 | Chen | 430/22 |
| 2006/0256338 A1 * | 11/2006 | Gratton et al. | 356/417 |

* cited by examiner

*Primary Examiner*—Roy M Punnoose
*Assistant Examiner*—Michael Lapage
(74) *Attorney, Agent, or Firm*—Cardinal Law Group

(57) ABSTRACT

An optical detection system for a microfluidic device and a dry-focus microfluidic device compatible with the compact optical detection system are described. The system includes an LED; means for collimating light emitted by the LED; an aspherical, fused-silica objective lens; means for directing the collimated light through the objective onto a microfluidic device; and means for detecting a fluorescent signal emitted from the microfluidic device. The working distance between the objective and the device allows light from an external LED or laser to be brought in along a diagonal path to illuminate the microfluidic device. The dry-focus microfluidic device includes multiple channels and multiple closed optical alignment marks having curved walls. At least one of the channels is positioned between at least two of the marks. The marks are illuminated for alignment and focusing purposes by light brought in on a diagonal path from an external white LED.

20 Claims, 9 Drawing Sheets

COMPACT OPTICAL DETECTION SYSTEM FOR A MICROFLUIDIC DEVICE

RELATED APPLICATION

The present application claims priority to U.S. Provisional Patent Application Ser. No. 60/670,736, filed Apr. 12, 2005, entitled "Optical Detection for Microfluidic Devices," which is hereby incorporated by reference for all purposes as if set forth herein verbatim.

TECHNICAL FIELD

This invention relates generally to the field of detection optics. More specifically, the invention relates to a compact optical system for detecting fluorescent signals as well as a dry-focus microfluidic device compatible with the compact optical detection system.

BACKGROUND OF THE INVENTION

Currently existing optical detection systems for microfluidic devices are large, expensive, and inflexible. In existing microfluidic device instrumentation, the optical detection system is the costliest subsystem. The size, expense, and rigidity of current optical detection systems result largely from such systems employing multiple high quality lasers for fluorescence excitation, along with multiple charge-coupled device (CCD) cameras for detection.

Alignment and focusing of existing optical detection systems also presents problems. Typically, optics are aligned and focused by viewing fluorescent dye flowing through a channel in a microfluidic device. The dye must be allowed to reach the detection region of the microfluidic device before performing the alignment and focusing process. This can take several minutes for some microfluidic devices. In addition, the fluorescent dye is typically flushed out of the channel after focusing, a time-consuming and sometimes difficult process. Finally, the dye can be expensive and unstable, adding to the cost and complexity of the process.

Therefore, it would be desirable to provide an optical detection system as well as alignment and focusing means and methods that overcome the aforementioned and other disadvantages.

SUMMARY OF THE INVENTION

One aspect of the present invention is an optical detection system for a microfluidic device. The system comprises a light-emitting diode (LED); means for collimating the light emitted by the LED; an aspherical, fused-silica objective lens; means for directing the collimated light through the objective lens onto the microfluidic device; and means for detecting a fluorescent signal emitted from the microfluidic device. The system may include a second, external light source, which may be either an LED or a laser. The working distance from the objective lens to the microfluidic device may be sized to permit light from the LED or laser to be brought in along a diagonal path to illuminate the microfluidic device.

Another aspect of the present invention is a dry-focus microfluidic device. The device comprises a first substrate; multiple channels formed in the first substrate, at least one of which is a microfluidic channel; multiple optical alignment marks having curved walls that are formed in the first substrate spaced apart from the channels; and a second substrate bonded to the first substrate to form covered channels and closed optical alignment marks. At least one of the channels is positioned between at least two of the optical alignment marks.

The term "microfluidic" is used herein to define chambers and flow passages having cross-sectional dimensions on the order of 0.1 µm to 500 µm. The microfluidic flow channels and fluid handling regions have preferred depths on the order of 0.1 µm to 100 µm, typically 2.0 µm to 50 µm. The channels have preferred widths on the order of 2.0 µm to 500 µm, more preferably 3.0 µm to 100 µm. For many applications, channels of 5.0 µm to 50 µm widths will be useful. Chambers in the device often will have larger dimensions, e.g., a few millimeters.

The aforementioned and other features and advantages of the invention will become further apparent from the following detailed description of the presently preferred embodiments, read in conjunction with the accompanying drawings, which are not to scale. The detailed description and drawings are merely illustrative of the invention, rather than limiting, the scope of the invention being defined by the appended claims and equivalents thereof.

DETAILED DESCRIPTION OF THE PRESENTLY PREFERRED EMBODIMENTS

Figure 1:
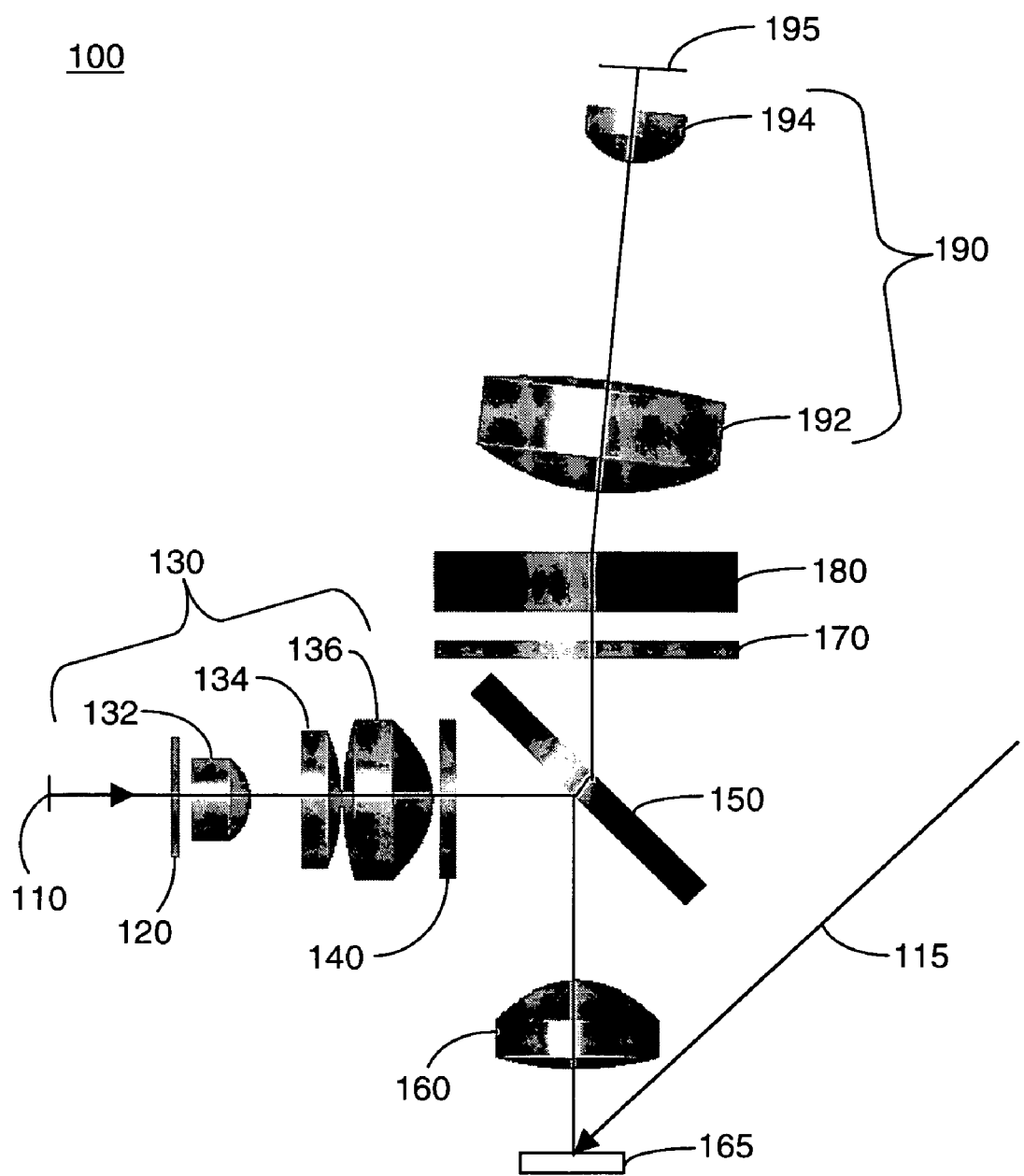
FIG. 1 is a schematic representation of one embodiment of an optical detection system according to the present invention.

One aspect of the present invention is an optical detection system. One embodiment of the system, in accordance with the present invention, is illustrated in FIG. 1 at 100. In the present nonlimiting example, system 100 comprises an LED light source 110; a slit 120; a slit lens 130 comprising three slit lens elements 132, 134, and 136; an excitation bandpass filter 140; a beam splitter 150, an objective lens 160; a rejection filter 170; a diffraction grating 180; a CCD lens 190 comprising CCD lens elements 192 and 194; and a CCD array 195. A second light source, which may be either a laser or an LED, is indicated at 115. A microfluidic device is indicated at 165.

Slit 120 is back illuminated by LED 110. The LED may be used in place of or in addition to a laser light source, as will be explained below. The size, shape, wavelength, and power level of the LED may be varied. LEDs are currently available in various colors, including UV, blue, cyan, and green, representing emission wavelengths of 400-750 nm. Multiple LEDs may be loaded into the system, e.g., placed in a rotating turret having a motorized mechanism, and selected for the fluorophore being detected.

Light from LED 110 passes through slit 120. The spectral resolution of the present embodiment is inversely proportional to the sensitivity, as is the case for any spectrometer. Therefore, placing a wider slit results in higher sensitivity but poorer color separation. For many assays, only two or three color bands may be required, thus allowing the slit to be set wider for high sensitivity.

After passing through slit 120, light from LED 110 is collected and collimated by slit lens 130, which compensates for axial color introduced at objective lens 160 as light travels through it toward device 165. The color corrector lenses are necessary to prevent the image of the slit cast upon the microfluidic device for excitation from becoming smeared out, causing a loss of spatial resolution. Color may be corrected for more than one wavelength range, in the present example 350-400 nm and 430-480 nm. The slit-to-lens distance is set differently for each range, for example through software controls available to the user.

Slit lens 130 comprises slit lens elements 132, 134, and 136. In the present example, each lens element is custom designed and made from a UV-transparent, dispersive glass. Slit lens 130 is designed for UV wavelengths emitted by UV LEDs. It works with objective lens 160 to form a sharp image of slit 120 on microfluidic device 165. Slit lens element 132 is made from Hoya glass type TAC6, and has an edge diameter of 14 mm and a center thickness of 10.9 mm. Slit lens element 134 is made from Hoya glass type NBFD12, and has a diameter of 23 mm and a center thickness of 3.14 mm. Slit lens element 136 is made of fused silica and is a duplicate of objective lens 160, which is described fully below.

Figure 2:
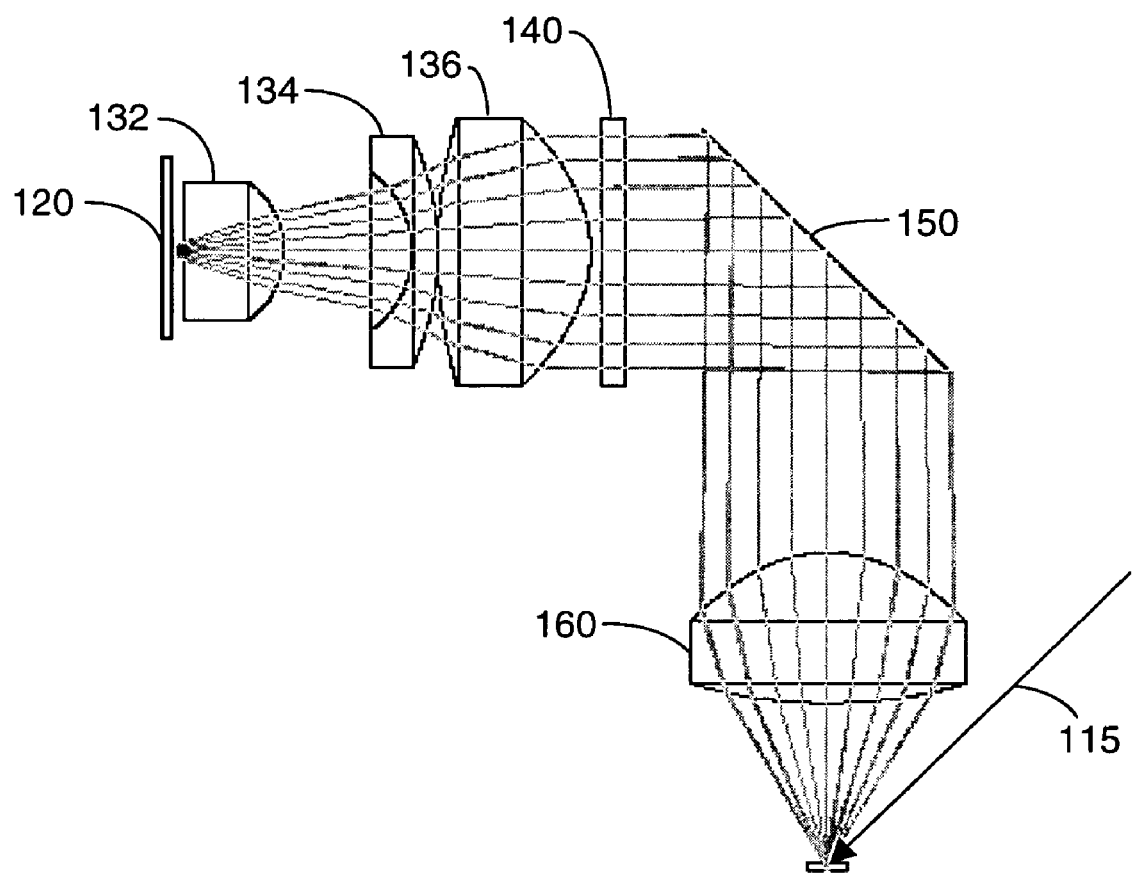
FIG. 2 illustrates the excitation optical path of the system of FIG. 1.

Excitation bandpass filter 140 attenuates frequencies outside the desired range before flat, dichroic beam splitter 150 (e.g., a dichroic mirror) directs the now collimated excitation light emitted by LED 110 down through objective lens 160 onto microfluidic device 165. The full excitation optical path is illustrated in FIG. 2.

Objective lens 160 is a high efficiency, custom-designed, fused-silica objective of 0.5 numerical aperture (NA), with a 60-degree total cone angle of collected light. As can be seen in FIG. 1, the objective must not only deliver excitation light, but also collect and collimate fluorescent light. Light collection efficiency goes approximately as the square of NA. The high collection efficiency of objective lens 160 enables the use of lower power, and hence less expensive, light sources such as LED 110.

Objective lens 160 is a single element of fused silica to reduce unwanted background fluorescence, which would limit assay sensitivity because the lens is used in epifluorescence mode. Because the lens is made of a single material with finite dispersion, its focal length is a slight function of wavelength. The lens has an edge diameter of 27 mm and a thickness of 15.02 mm. The edges of the lens are beveled at 45 degrees to an 0.5 mm maximum face width. The back surface of the lens is aspherical to correct spherical aberration. The system's aperture stop is located on the backside of the lens, with no vignetting from there to the CCD array.

Objective lens 160 was optimized at a single wavelength (550 nm) by modeling it with a paraxial lens with the image at the paraxial focus. The object plane was modeled to lie below 700 microns of a parallel plate made of fused silica, i.e., the top of the microfluidic device. Thus the objective was optimized to form an image at infinity. All object field points were weighted equally.

In the present example, the working distance from objective lens 160 to microfluidic device 165 is 16 mm. The objective's diameter (27 mm) and working distance allow clearance for external laser beam illumination brought in at, for example, a 45-degree angle. A variety of lasers can be used in conjunction with embodiments of the invention. For example, a blue LED may be coupled with a red laser. One LED and one or more laser beams brought in collinearly can be used at the same time. As will be discussed in detail below, light from a second LED may also be brought in externally along a diagonal path for alignment and focusing purposes. Light source 115 represents either a laser or an LED light source.

The working distance from objective lens 160 to microfluidic device 165 also offers a wide (3.4-mm) field of view, allowing fluorescence measurement in up to 16 channels pitched at 200 microns or 20 channels pitched at 150 microns.

Figure 3:
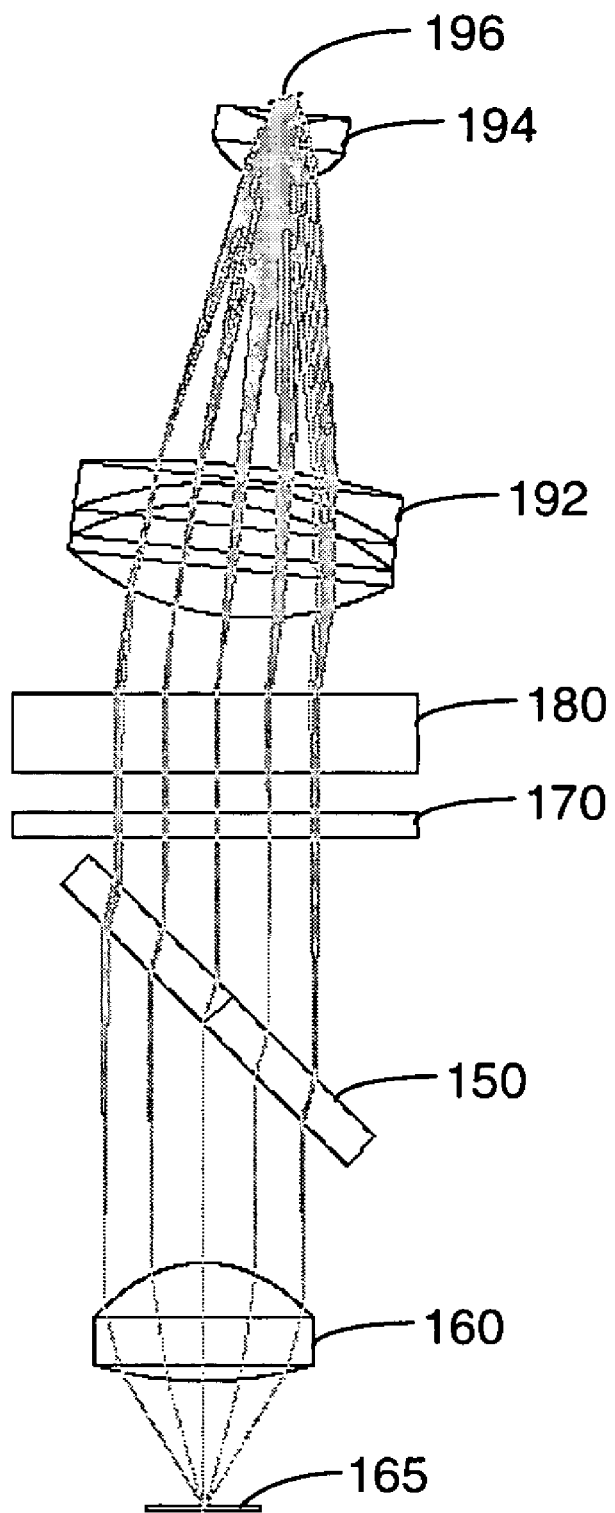
FIG. 3 illustrates the detection optical path of the system of FIG. 1.

The full detection optical path is illustrated in FIG. 3. System 100 accommodates emission wavelengths ranging between 400 nm and 750 nm. As can be seen, the fluorescent signal(s) emitted from microfluidic device 165 pass through dichroic mirror 150 with minimal reflection. Rejection filter 170 prevents excitation light from being transmitted along the detection path.

Following rejection filter 170 in the detection path is diffraction grating 180, which is an anti-reflection coated BK7 blazed diffraction grating used for dispersing the fluorescent light into its constituent colors so they can be detected independently. The grating blaze angle is chosen to optimize the transmission of visible light into the first order. The zero$^{th}$ and second orders are, preferably, not cast onto CCD array 196.

Because objective lens 160 is a singlet, it introduces chromatic aberrations, primarily in the form of axial color. These aberrations are corrected at CCD lenses 192 and 194. The axial color is also partly corrected by tilting CCD array 196 as well as CCD lenses 192 and 194. The rotation angle is restricted to less than 15 degrees off-normal. Tilting CCD array 196 corrects the axial colors because the colors are spread across the CCD array with diffraction grating 180.

CCD lens 190 comprises CCD lens elements 192 and 194. Lens element 192 is a field lens with an edge diameter of 16.5 mm and a thickness of 7.63 mm. CCD lens element 194 is a triplet of various glasses chosen for their dispersive properties. The CCD lenses need not be made of low fluorescence glass because excitation light does not pass through them. CCD lens 194 has an overall edge diameter of 40 mm and thicknesses of 14.0 mm, 2.5 mm, and 2.5 mm for the three portions of the lens.

CCD array 195 serves as a detector. In the present example, the format of the array is 658×496 pixels, with 7.4-micron pixel size. Pixel grouping is programmable through a software interface. Before the detector is used in an actual experiment, the user is able to select the desired detection bands. The detection bands typically correspond to the location of channels on microfluidic device 165. As noted previously, the present embodiment was designed to induce and read fluorescence from up to 16 channels pitched 200 microns apart or 20 channels pitched 150 microns apart. The detection bands employed by the detector can be aligned with the channels using techniques described below. During the course of an experiment, the detector output will be a two-dimensional array with the channels forming one axis of the array, while the detected colors form the other axis. For example, a system designed to detect green and red fluorescence emanating from 12 channels in a microfluidic device would output a 12×2 array.

One skilled in the art will appreciate that an optical detection system according to the present invention may be varied in numerous ways. For example, design parameters of the lenses used in the system may be varied, including diameter, numerical aperture, focal length, and material, with the exception that the objective lens is preferably fused silica. Light sources may also vary, with different combinations of CCD and laser light sources being used. The format of the CCD array may vary as well.

Figure 4:
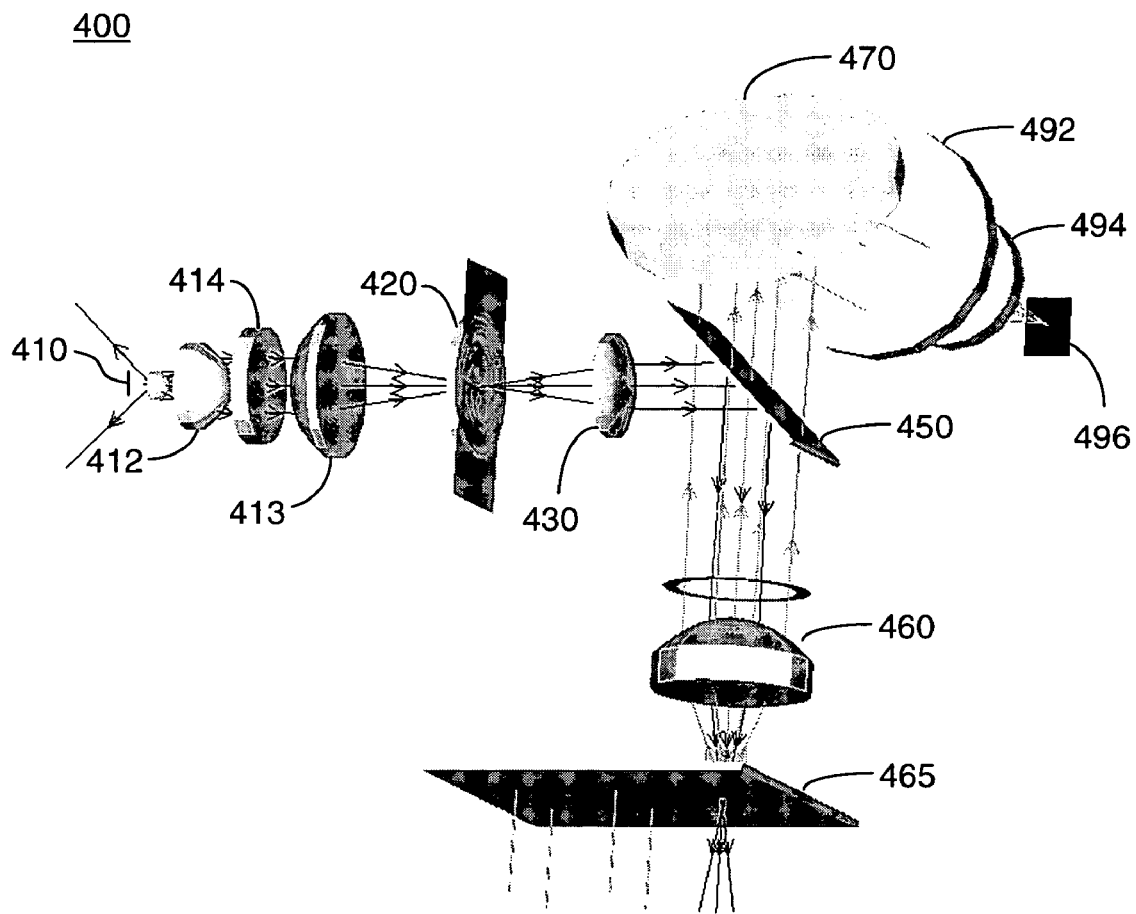
FIG. 4 is a schematic representation of another embodiment of an optical detection system according to the present invention.

Other changes may be made as well. For example, FIG. 4 illustrates an alternative and even less expensive embodiment that is not multispectral. This nonlimiting example uses commercially available components with the custom-designed, high-numerical-aperture objective lens described above. System 400 comprises an LED light source 410, condenser lenses 412 and 414 separated by an excitation bandpass filter 413, a slit 420, a single slit lens 430, a beam splitter 450, custom-designed high-numerical-aperture objective lens 460, a folding mirror 470, and a CCD lens 492 separated from a CCD array 496 by an emission bandpass filter 494. The working distance between objective lens 460 and the microfluidic device, shown at 465 in FIG. 4, is similar to that in the previous example, allowing the system to be used with a laser as well as an LED. Both excitation and detection optical paths are shown in FIG. 4.

LED light source 410 is a blue LED (e.g., a Cree XLamp 7090 LED). Condenser lens 412 is a 15-mm diameter lens with an effective focal length of 12 mm, fabricated using B270 glass with a single-layer $MgF_2$ coating (e.g., from Newport Corp.). Lens 412 has an effective focal length of 12 mm. Condenser lens 414 is a 25-mm diameter lens fabricated using BK7 glass with a ¼-wave $MgF_2$ coating (e.g., from Edmund Optics). Lens 414 has an effective focal length of 30 mm. Excitation bandpass filter 413 is fabricated from NBK7 glass to have a center wavelength of 470 nm, a diameter of 25 mm, and a thickness of 5 mm (e.g., from Semrock).

Slit 420 is a 500-micron chromium-coated soda lime glass slit with a diameter of 25.4 mm and a thickness of 1.5 mm (e.g., from Lenox Laser). Slit lens 430 is an 18-mm diameter lens with an effective focal length of 27 mm, fabricated using SF5 glass with a ¼-wave $MgF_2$ coating (e.g., from Edmund Optics).

Beam splitter 450 is an extended-band dichroic beam splitter (e.g., from Semrock). Objective lens 460 is the custom-designed, high-numerical-aperture objective lens that is also illustrated at 160 and was described previously. Folding mirror 470 is a standard, commercially available folding mirror.

CCD lens 492 is, e.g., a Nikon 50-mm f1.4 lens used with a Rolera-XR CCD camera, i.e., CCD array 496. Emission bandpass filter 494 is fabricated from NBK7 glass to have a center wavelength of 531 nm, a diameter of 25 mm, and a thickness of 5 mm (e.g., from Semrock).

In practice, an optical detection system in accordance with the present invention offers a number of advantages over existing systems. For example, the lens layout allows excitation light to be delivered both axially, as in epifluorescence systems, or externally at an oblique angle. The high numerical aperture of the custom, fused-silica objective lens permits the use of a lower power and less expensive light source in the form of an LED. For example, a blue LED costs about $25, while a blue laser costs about $10,000. The lens system also allows the use of a single CCD, rather than multiple CCDs, for additional cost savings. In addition to being less expensive than typical optical detection systems, the described system is more compact. Because of the low cost and small size of systems in accordance with the invention, several LEDs of various colors may be incorporated into a system such as that seen in FIG. 1, thus providing built-in flexibility of excitation colors. Detection wavelengths may be set through software controls available to the user.

Another advantage of an optical detection system according to the present embodiment is that light from a second LED can be delivered externally at an oblique angle to the microfluidic device for alignment and focusing purposes. To solve problems associated with the use of flowing fluorescent dyes, an optical detection system such as has been described above may be combined with a dry-focus microfluidic device to form an analytical unit.

Figure 5:
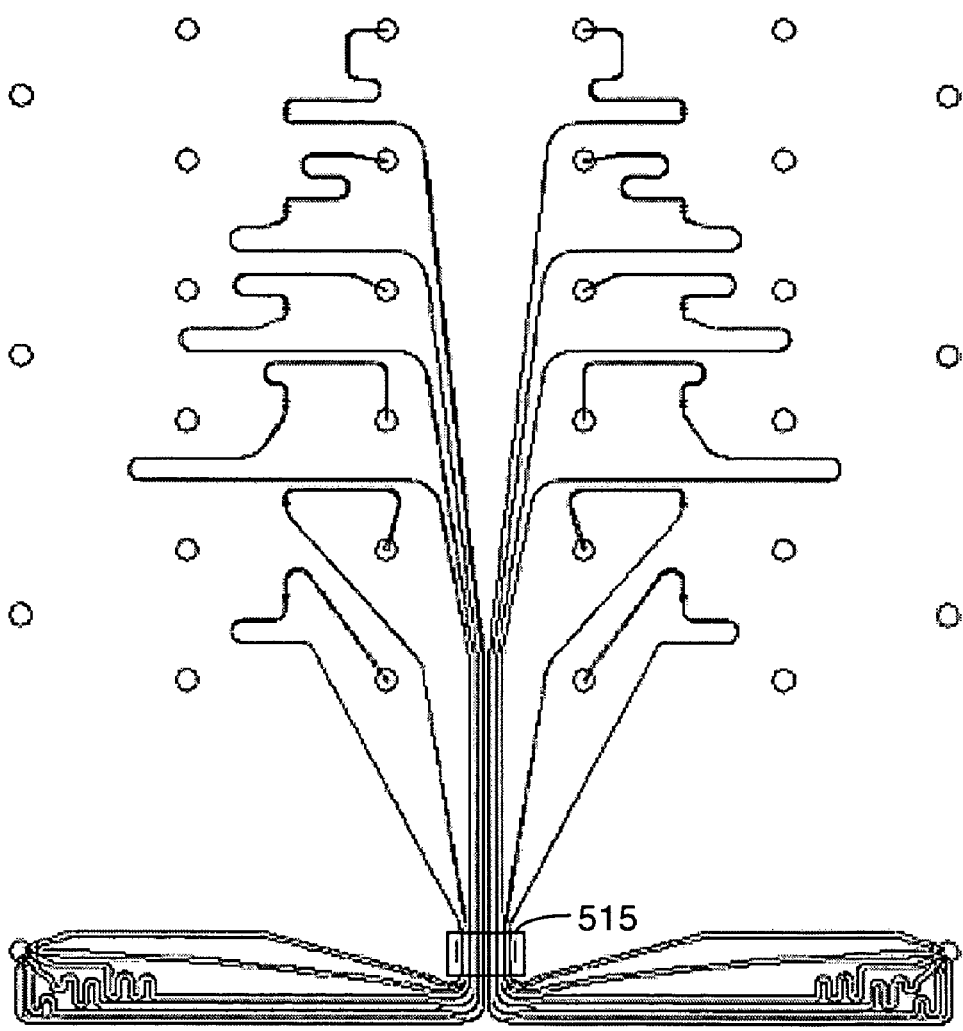
FIG. 5 is a schematic representation of one embodiment of a dry-focus microfluidic device according to the present invention.

One embodiment of the dry-focus microfluidic device, in accordance with the present invention, is illustrated at 500 in FIG. 5. One skilled in the art will appreciate that the number and arrangement of chambers and flow passages may vary, depending on the intended use for the device. At least one channel of the dry-focus device is microfluidic.

Figure 6:
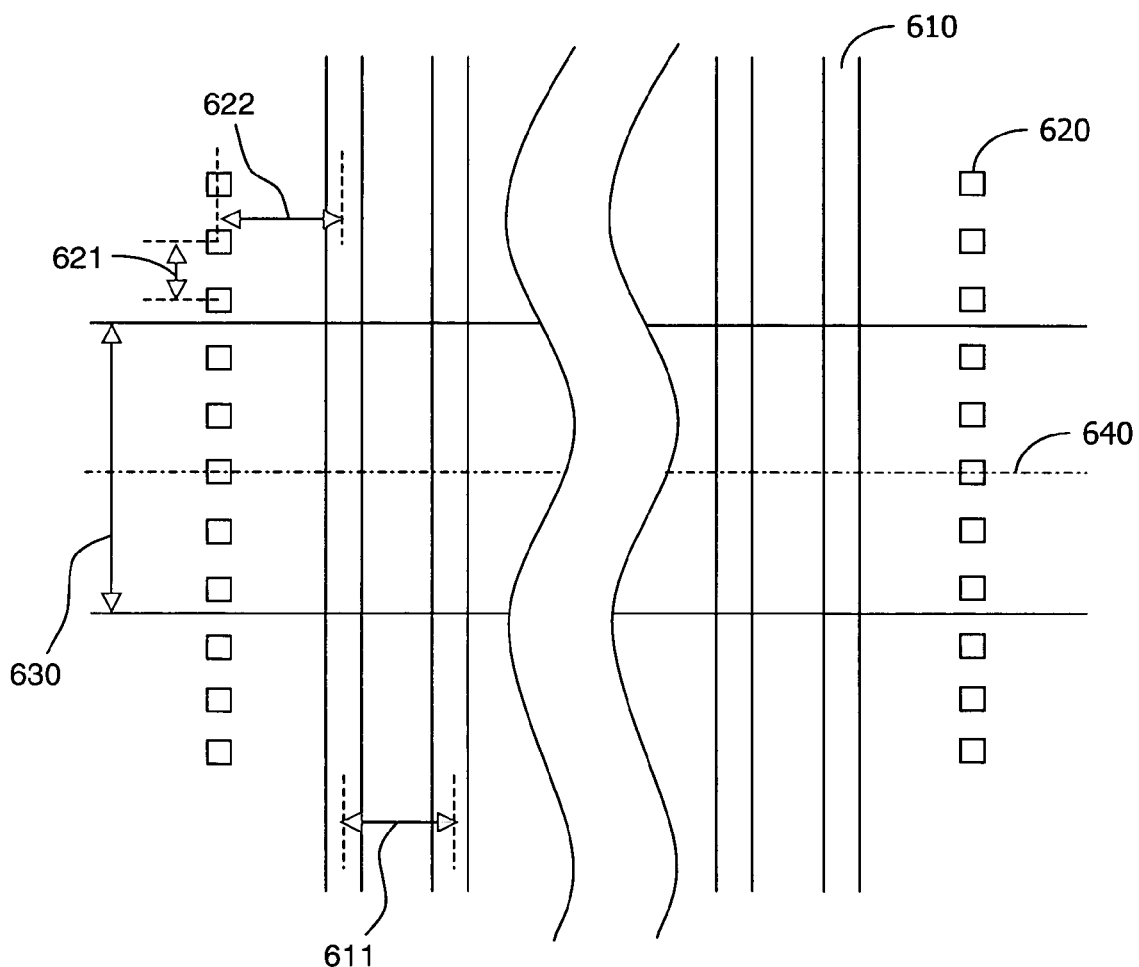
FIG. 6 illustrates an enlarged schematic representation of a detection region of the device of FIG. 5.

A detection region 515 of FIG. 5 is seen enlarged in FIG. 6. While detection region 515 includes 12 channels and a total of 22 optical alignment marks arranged in two arrays positioned parallel to and to the outside of the channels, 11 marks per array, the number of channels shown in FIG. 6 has been reduced to four to allow better visualization of the individual elements. As illustrated in FIG. 6, the spacing 611 between channels 610 (i.e., the channel pitch) is 200 microns for 12 or fewer channels, and 150 microns for 13 to 16 channels. The spacing 621 between marks 620 is 100 microns. The distance between marks 620 and an adjacent channel 610, indicated at 622, is at least 200 microns, regardless of the number and pitch of the channels. Nominal illumination length 630 is 500 microns. The nominal detection center is shown at 640.

Channels are typically etched into a substrate using standard photolithographic methods known in the art. Alignment marks are also etched into the substrate and may be the same depth as the channels. In the present embodiment, marks 620 are formed using a square, 10×10 micron mask feature, resulting in an alignment mark somewhat larger than the mask feature. An isotropic etch is used in fabricating alignment marks 620, resulting in a mark with a flat base and curved walls. See, for example, FIG. 7, which shows a cross-sectional view of an individual alignment mark 620. A second substrate or cover 625 is typically bonded to the etched substrate, forming covered channels 610 and closed optical alignment marks 620.

Figure 7:
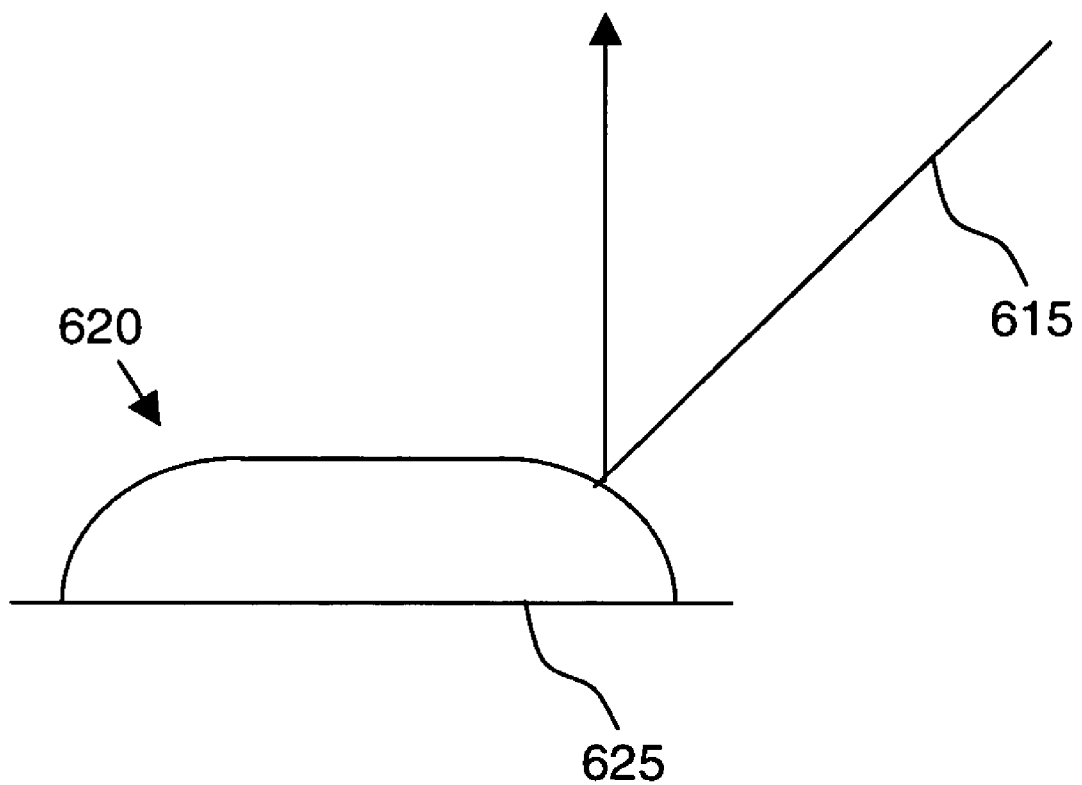
FIG. 7 is a cross-sectional view of an individual alignment mark according to the present invention.

A white LED is used to illuminate alignment marks 620. Light 615 from the LED is brought in externally along a diagonal path. As previously noted, an optical detection system such as has been described above is configured with the objective lens spaced above the device to allow for this diagonal path. As indicated in FIG. 7, the microfluidic device is positioned for illumination and detection with the base of the alignment mark nearest the optics. Light 615 from the white LED reflects off the curved wall at an angle that directs the light into the objective lens of the optical detection system. Because the device surfaces are virtually flat, light delivered at an oblique angle is not reflected from these surfaces into the objective lens. Channels etched at the same time as the alignment marks and, therefore, having the same curve, are virtually invisible because they are filled with a liquid, which allows light to pass through the channel wall rather than being reflected off the curved wall. One skilled in the art is aware that microfluidic devices are typically primed with a buffer or other liquid prior to use.

Figure 8A:
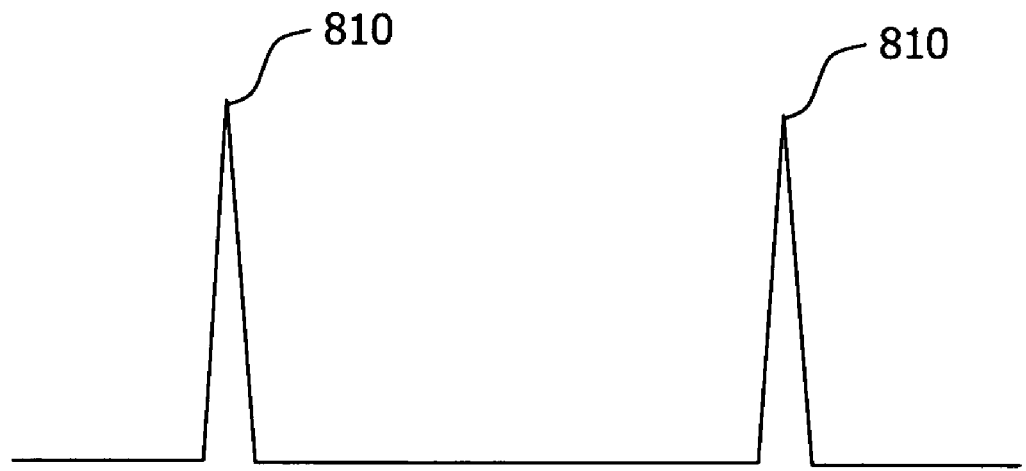
FIGS. 8A and 8B illustrate optical signals such as would be generated by the two arrays of alignment marks illustrated in FIG. 6.
Figure 8B:
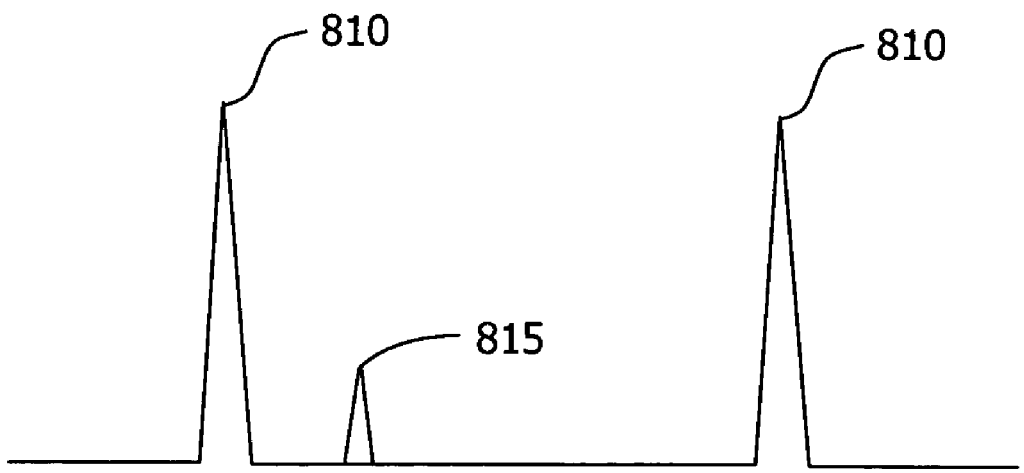

FIG. 8A shows an optical signal such as would be generated by the two arrays of alignment marks that are described above and illustrated in FIG. 6. As can be seen, each array produces a distinct peak 810. While an array may include any number of alignment marks, one skilled in the art will appreciate that the use of multiple alignment marks is preferable in order to produce a peak that is easily distinguished from a peak produced by a speck of dust or other small defect on or in the microfluidic device. FIG. 8B, shows alignment marks 810 as well as a peak 815 produced by a defect on or in the device. As can be seen, peaks produced by the arrays of alignment marks 810 are significantly higher than the peak 815 produced by the defect.

With distinct alignment peaks such as are seen in FIGS. 8A and 8B, an autofocus algorithm may simply search for the two highest peaks. Because the autofocus algorithm has been provided data regarding the distance between the two arrays of alignment marks as well as the distance from each array to the adjacent channel and the pitch of the channels, the optical detection system can be focused and aligned to the alignment marks and then displaced the appropriate distance to align to a microfluidic channel. Thus, the autofocus algorithm can be made robust against defects by rejecting small peaks and by verifying spacing between expected peaks.

One skilled in the art will appreciate that a dry-focus microfluidic device in accordance with the present invention may be varied in numerous ways. For example, embodiments of the invention could be employed for single-channel as well as multichannel microfluidic devices. Control of the alignment and focusing could be manual rather than being automatically controlled by an autofocus algorithm. Alignment marks need not be etched, but may be formed by other processes such as stamping, embossing, molding, and laser ablating a substrate. The number of marks may be varied. The shape of the marks may be varied as well; however, the shape and size were optimized for the embodiment described above. The depth of the marks is not critical and may be varied. The exact location along the direction parallel to the channels is also not critical. Placement of the marks with relation to the channels may vary as well, provided the marks are not positioned so close to the channels that the integrity of the channels is put at risk. A number of different wavelengths of light could be used to illuminate the optical alignment marks. In addition, a solid-state fluorescent material could be placed within the optical alignment marks to increase the optical signal produced by the marks.

Figure 9:
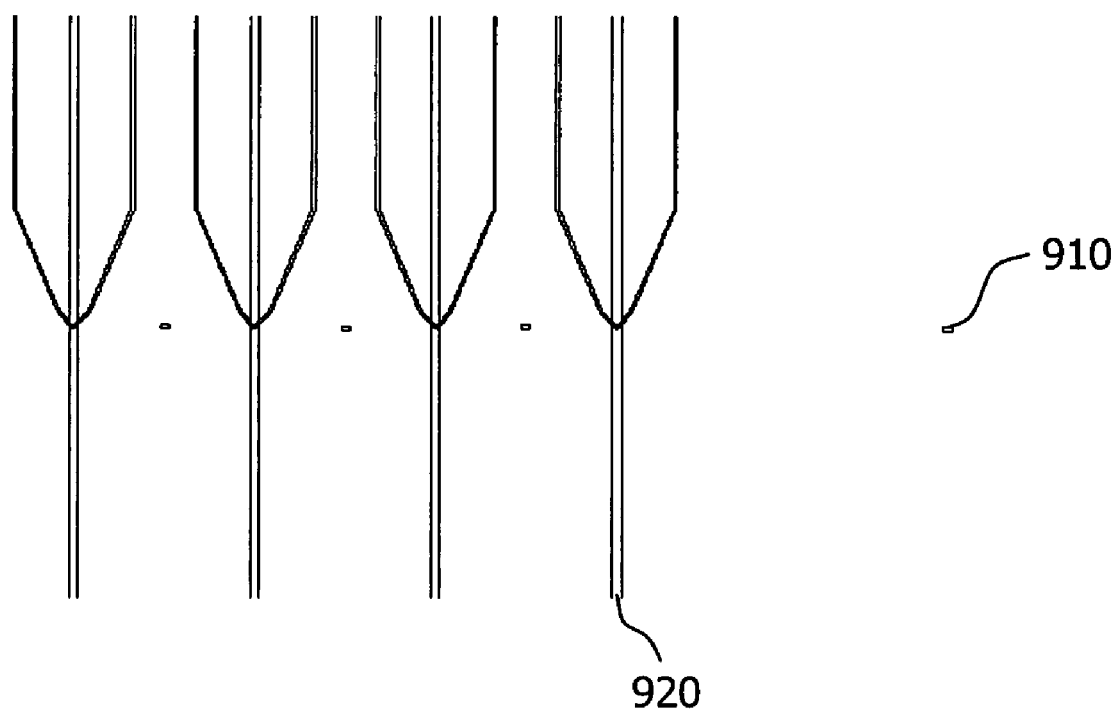
FIG. 9 is a schematic representation of another embodiment of a dry-focus microfluidic device according to the present invention.

A variety of different patterns may be used for the optical alignment marks. For example, FIG. 9 shows an alternative embodiment having a pattern in which alignment marks 910 are positioned between each of four channels 920 as well as outside each outer channel. Each of the four channels branches into three channels in the top half of the figure.

Another aspect of the present invention is a method for aligning and focusing an optical detection system. A microfluidic device having a plurality of channels and a plurality of optical alignment marks is provided. At least one of the channels is microfluidic. Preferably the optical alignment marks were formed by etching the marks into a substrate using an isotropic etch and a square, 10×10 micron mask feature. The device is positioned relative to the optics of the optical detection system with the bottoms of the optical alignment marks nearer to the optics than are the tops of the marks. The light from an external white LED is brought in at an oblique angle to illuminate the optical alignment marks. Data collection for the optical detection system is set to line mode. The system is aligned using light reflected from the optical alignment marks. The system is focused using light reflected from the optical alignment marks. Data obtained regarding the position of the optical alignment marks is combined with data resident in the optical detection system regarding spacing of the optical alignment marks relative to the channels to position the optical detection system to sense fluorescent signals from the channels.

Embodiments of the invention offer a number of advantages over previously known methods and apparatuses. One advantage is that the invention does not require flowing dye through channels to perform optical alignment and focusing. Not flowing dye eliminates the use of expensive and unstable dyes, removes the need to wait for dye breakthrough, and removes the need to flush out dye after alignment and focusing.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A dry-focus microfluidic device, comprising:
   a first substrate;
   a plurality of channels formed in the first substrate, wherein at least one channel is a microfluidic channel;
   a plurality of optical alignment marks formed in the first substrate spaced apart from the plurality of channels, each alignment mark having a curved wall; and
   a second substrate bonded to the first substrate such that the channels are covered and the alignment marks are closed;
   wherein at least one channel is positioned between at least two alignment marks.

2. The device of claim 1 wherein the optical alignment marks form two arrays, wherein the plurality of channels includes at least two parallel channels, and wherein the parallel channels are positioned between the two arrays.

3. The device of claim 1 wherein the device includes at least 12 parallel channels and at least 22 optical alignment marks, the alignment marks forming two arrays, the arrays positioned parallel to and outside of the channels.

4. The device of claim 1 wherein the curved wall of each optical alignment mark is reflective to light brought in at an oblique angle to the device, the wall being configured such that the path of the reflected light is substantially orthogonal to the device.

5. An optical detection system for a microfluidic device, comprising:
   a microfluidic device comprising:
      a first substrate;
      a plurality of channels formed in the first substrate, wherein at least one channel is a microfluidic channel;
      a plurality of optical alignment marks formed in the first substrate spaced apart from the plurality of channels, each alignment mark having a curved wall;
      a second substrate bonded to the first substrate such that the channels are covered and the alignment marks are closed;
      wherein at least one channel is positioned between at least two alignment marks;
   a light-emitting diode;
   means for collimating light emitted by the light-emitting diode;
   an aspherical, fused-silica objective lens;
   means for directing the collimated light through the objective lens onto the microfluidic device; and
   means for detecting a fluorescent signal emitted from the microfluidic device.

6. The system of claim 5 wherein the collimating means comprise a slit and a slit lens.

7. The system of claim 5 wherein the directing means comprise a dichroic beam splitter.

8. The system of claim 5 wherein the detecting means comprise a CCD.

9. The system of claim 8 further comprising a CCD lens, wherein the CCD lens comprises a triplet lens element.

10. The system of claim 5 further comprising one or more of a condenser lens, an excitation bandpass filter, a rejection filter, a diffraction grating, a beam splitter, a folding mirror, and an emission bandpass filter.

11. The system of claim 5 wherein the light emitted by the LED is delivered axially to the microfluidic device.

12. The system of claim 5 farther comprising an external light source.

13. The system of claim 12 wherein a working distance from the objective lens to the microfluidic device is sized to permit illumination of the microfluidic device by light delivered at an oblique angle from the external light source.

14. The system of claim 12 wherein the external light source is one of a light-emitting diode and a laser.

15. The system of claim 12 wherein the alignment marks are illuminated by the external light source.

16. The system of claim 15 wherein the external light source is a white LED.

17. The system of claim 15 further comprising a computer-usable medium that includes a program comprising an auto-focus algorithm.

18. The system of claim 17 wherein the computer-usable medium includes computer program code for setting detection wavelengths.

19. A method for aligning and focusing an optical detection system, comprising:

provilding a microfluidic device having a plurality of optical alignment marks and a plurality of channels etched into a substrate, wherein at least one of the channels is a microfluidic channel;

positioning the device relative to optics of the optical detection system such that the bottoms of the optical alignment marks are nearer to the optics than are the tops of the marks;

bringing light from an external white LED in at an oblique angle to illuminate the optical alignment marks;

setting data collection for the optical detection system to a line mode wherein the system scans in a line during detection;

aligning the optical detection system using light reflected from the optical alignment marks;

focusing the optical detection system using light reflected from the optical alignment marks; and combining data collected in line mode regarding the optical alignment marks with data resident in the optical detection system regarding spacing of the optical alignment marks relative to the channels to position the optical detection system to sense fluorescent signals from the channels.

20. The method of claim 19 wherein the optical alignment marks are etched into the substrate using an isotropic etch and a square, 10×10 micron mask feature.

* * * * *